United States Patent
Cohen et al.

(10) Patent No.: US 10,529,119 B2
(45) Date of Patent: *Jan. 7, 2020

(54) FAST RENDERING OF QUADRICS AND MARKING OF SILHOUETTES THEREOF

(71) Applicant: BIOSENSE WEBSTER (ISRAEL) LTD., Yokneam (IL)

(72) Inventors: Benjamin Cohen, Haifa (IL); Natan Sharon Katz, Atlit (IL); Lior Zar, Poria Illit (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/839,039

(22) Filed: Dec. 12, 2017

(65) Prior Publication Data

US 2018/0182159 A1 Jun. 28, 2018

Related U.S. Application Data

(63) Continuation-in-part of application No. 15/390,509, filed on Dec. 25, 2016.

(51) Int. Cl.
  *G06T 15/06* (2011.01)
  *G06T 15/20* (2011.01)
  *G06T 15/40* (2011.01)
  *G06T 17/20* (2006.01)

(52) U.S. Cl.
  CPC .............. *G06T 15/06* (2013.01); *G06T 15/20* (2013.01); *G06T 15/40* (2013.01); *G06T 17/205* (2013.01)

(58) Field of Classification Search
  None
  See application file for complete search history.

(56) References Cited

U.S. PATENT DOCUMENTS

| | | | |
|---|---|---|---|
| 4,615,013 | A | 9/1986 | Yan et al. |
| 5,760,786 | A | 6/1998 | Marks et al. |
| 6,377,259 | B1 | 4/2002 | Tenev et al. |
| 6,400,365 | B1 | 6/2002 | Setoguchi |

(Continued)

OTHER PUBLICATIONS

Bosch, Marc Ten, "CS400 assignment 3 Intersection writeup: Quadric Surfaces", Dec. 15, 2004, pp. 1-2.

(Continued)

*Primary Examiner* — Tize Ma
(74) *Attorney, Agent, or Firm* — Dergosits & Noah LLP; Todd A. Noah

(57) ABSTRACT

Described embodiments include an apparatus that includes a display, including a screen, and a processor. The processor is configured to define a bounding region on the screen. The processor is further configured to render a quadric, which is defined in a parameter space, over a three-dimensional electroanatomical map of a surface of a heart that is displayed on the screen, by, for each pixel in the bounding region, transforming, to the parameter space, a virtual ray that passes through the pixel, and ascertaining whether a point of intersection between the transformed virtual ray and the quadric exists in the parameter space, and, for each pixel in the bounding region for which the point of intersection exists, rendering the pixel on the screen, based on properties of the point of intersection. Other embodiments are also described.

24 Claims, 6 Drawing Sheets

(56) References Cited

U.S. PATENT DOCUMENTS

| | | |
|---|---|---|
| 6,614,428 B1 | 9/2003 | Lengyel |
| 6,791,543 B2 | 9/2004 | Kawanaka |
| 6,900,818 B1 | 5/2005 | Moffitt |
| 7,466,314 B2 | 12/2008 | Loop et al. |
| 7,952,583 B2 | 5/2011 | Waechter et al. |
| 8,717,357 B2 | 5/2014 | McCombe et al. |
| 9,159,162 B2 | 10/2015 | Carbonera et al. |
| 9,214,038 B1 | 12/2015 | Urbach |
| 2002/0059042 A1 | 5/2002 | Kacyra et al. |
| 2004/0184013 A1 | 9/2004 | Raskar et al. |
| 2007/0097121 A1 | 5/2007 | Loop et al. |
| 2012/0172724 A1 | 7/2012 | Hill et al. |
| 2012/0256915 A1 | 10/2012 | Jenkins |
| 2017/0285791 A1* | 10/2017 | Tu .......................... B60K 35/00 |

OTHER PUBLICATIONS

Garland, Michael et al., "Surface Simplification Using Quadric Error Metrics", Computer Graphics Proceedings, Annual Conference Series, Carnegie Mellon University, 1997, pp. 209-216.

Oliveira, Manuel M. et al., "An Efficient Representation for Surface Details", UFRGS, Technical Report RP-351, Jan. 26, 2005.

Sigg, Christian et al., "GPU-Based Ray-Casting of Quadratic Surfaces", Eurographics Symposium on Point-Based Graphics (2006), The Eurographics Association.

European Search Report for European Patent Application No. 17210088.5, dated Mar. 18, 2018.

European Search Report for European Patent Application No. 17210078.6, dated Mar. 18, 2018.

Carsten Stoll et al., "Incremental Raycasting of Piecewise Quadratic Surfaces on the GPU", IEEE Symposium on Interactive Ray Tracing, IEEE, Salt Lake City Utah USA dated Sep. 1, 2006, pp. 141-150.

"Murat D. Aykin et al, ""Efficient Ray-casting of Quadric Surfaces for Forward-Scan Sonars""", Oceans 2016 MTS/IEEE Monterey, Sep. 19-23, 2016 , Monterey, CA, USA."

Non-Final Office Action for U.S. Appl. No. 15/390,509, dated Mar. 7, 2018.

\* cited by examiner

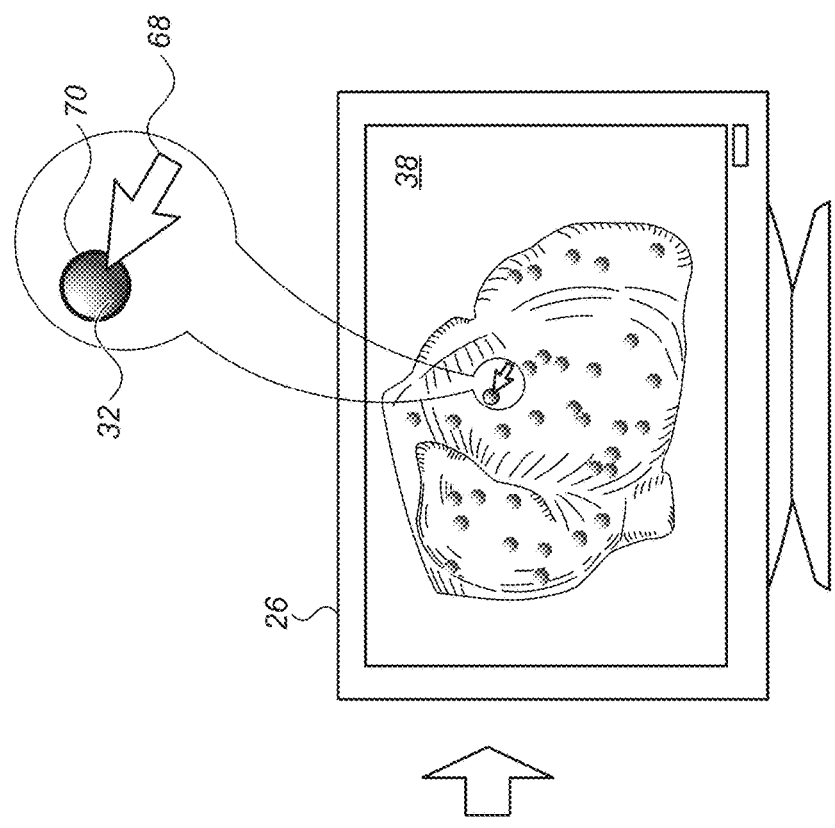
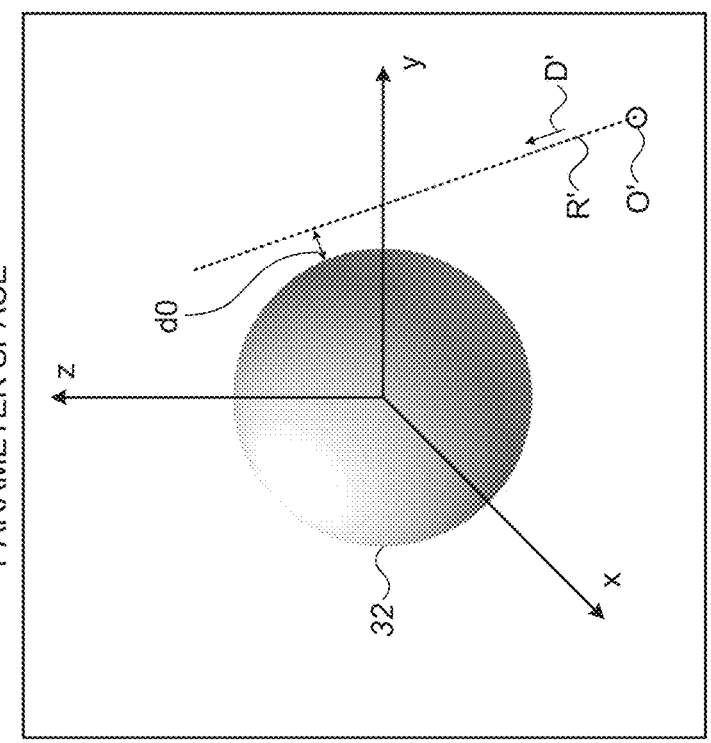
FIG. 4

FAST RENDERING OF QUADRICS AND MARKING OF SILHOUETTES THEREOF

CROSS-REFERENCE TO RELATED APPLICATION

The present application is a continuation-in-part of, and claims the benefit of, U.S. application Ser. No. 15/390,509, entitled "Fast rendering of quadrics," filed Dec. 25, 2016, whose disclosure is incorporated herein by reference.

FIELD OF THE INVENTION

The present invention relates to the field of computer graphics, and especially to the rendering of quadrics.

BACKGROUND

In a rendering technique known as ray casting, a computer simulates the casting of rays onto a virtual scene, and renders the scene in accordance with the interaction between these rays and objects in the scene.

In some rendering applications, objects in the virtual scene are modeled as quadratic surfaces, or "quadrics." The equation for a quadric may be expressed in homogenous (x,y,z,w) coordinates as $Ax^2+2Bxy+2Cxz+2Dxw+Ey^2+2Fyz+2Gyw+Hz^2+2Izw+Jw^2=0$. More compactly, this may be written in matrix form as $X^TQX=0$, where $$X = \begin{matrix} x \\ y \\ z \\ w \end{matrix} \text{ and } Q = \begin{matrix} A & B & C & D \\ B & E & F & G \\ C & F & H & I \\ D & G & I & J \end{matrix}.$$

(Generally, w is set to 1.) Examples of quadric surfaces include spheres, ellipsoids, cylinders, cones, hyperbolic paraboloids, paraboloids, and hyperboloids.

A ray may be expressed by the equation $R=O+tD$, where R is any point on the ray, O is the origin of the ray, D is the direction vector of the ray, and t is a scalar parameter. R, O, and D may be expressed in homogenous coordinates.

Sigg, Christian, et al., "GPU-Based Ray-Casting of Quadratic Surfaces," SPBG, 2006, which is incorporated herein by reference, proposes an efficient rendering technique for quadric primitives based on GPU-accelerated splatting.

SUMMARY OF THE INVENTION

There is provided, in accordance with some embodiments of the present invention, apparatus that includes a display, including a screen, and a processor. The processor is configured to define a bounding region on the screen, and to render a quadric, which is defined in a parameter space, over a three-dimensional electroanatomical map of a surface of a heart that is displayed on the screen, by, for each pixel in the bounding region, transforming, to the parameter space, a virtual ray that passes through the pixel, and ascertaining whether a point of intersection between the transformed virtual ray and the quadric exists in the parameter space, and, for each pixel in the bounding region for which the point of intersection exists, rendering the pixel on the screen, based on properties of the point of intersection.

In some embodiments, the processor is further configured to mark a silhouette of the quadric on the screen, by, for each pixel in the bounding region for which the point of intersection does not exist:
estimating a shortest distance between the transformed virtual ray and the quadric, and
provided that the estimated shortest distance is less than a threshold, marking the pixel as belonging to the silhouette.

In some embodiments, the processor is configured to mark the silhouette of the quadric in response to a user selecting the quadric on the screen.

In some embodiments, for each pixel in the bounding region for which the point of intersection does not exist, the processor is configured to:
ascertain that the point of intersection does not exist, by:
substituting an equation of the transformed virtual ray into an equation of the quadric, such as to yield a quadratic equation $at^2+bt+c=0$, and
ascertaining that a discriminant $b^2-4ac$ of the quadratic equation is negative, and
in response to ascertaining that the point of intersection does not exist, estimate the shortest distance between the transformed virtual ray and the quadric as $|c-b^2/4a|$.

In some embodiments, the processor is further configured to define the quadric, in the parameter space, such that the quadric is bounded by a cube having eight corners, two of which are at (−1,−1,−1) and (1,1,1), respectively.

In some embodiments, the processor is configured to define the bounding region by:
transforming the corners of the cube to a screen space, which is defined in terms of a coordinate system of the screen, and
defining the bounding region such that the bounding region is a minimum bounding rectangle of the transformed corners.

In some embodiments, the processor is further configured to define the quadric such that the quadric is representable by a 4×4 diagonal matrix Q.

In some embodiments,
the virtual ray has a ray origin O and a ray-direction vector D,
the processor is configured to transform the virtual ray by computing O', which is the ray origin O transformed to the parameter space, and D', which is the ray-direction vector D transformed to the parameter space, and
the processor is configured to ascertain whether the point of intersection exists by:
computing a first coefficient $a=D'^TQD'$, where $D'^T$ is a transpose of D', a second coefficient $b=2D'^TQO'$, and a third coefficient $c=O'^TQO'$, and
subsequently, ascertaining whether a quadratic equation $at^2+bt+c=0$ has any real roots.

In some embodiments, the processor is further configured to represent Q as a four-element vector $Q_D$, and the processor is configured to compute each of the first coefficient a, the second coefficient b, and the third coefficient c by performing an element-wise multiplication of $Q_D$.

In some embodiments, the processor is further configured to receive a signal that indicates a location of a distal end of an intrabody catheter, and the processor is configured to render the quadric over a portion of the three-dimensional electroanatomical map that corresponds to the indicated location.

In some embodiments, the processor is configured to render the quadric in response to an ablating signal being passed into the surface of the heart, by the distal end of the intrabody catheter, at the indicated location.

In some embodiments, the processor is configured to render the pixel on the screen by:
computing a normal vector to the quadric at the point of intersection, and rendering the pixel, based on a coloring of the quadric at the point of intersection, and the normal vector.

There is further provided, in accordance with some embodiments of the present invention, a method that includes, using a processor, defining a bounding region on a screen. The method further includes rendering a quadric, which is defined in a parameter space, over a three-dimensional electroanatomical map of a surface of a heart that is displayed on the screen, by, for each pixel in the bounding region, transforming, to the parameter space, a virtual ray that passes through the pixel, and ascertaining whether a point of intersection between the transformed virtual ray and the quadric exists in the parameter space, and, for each pixel in the bounding region for which the point of intersection exists, rendering the pixel on the screen, based on properties of the point of intersection.

There is further provided, in accordance with some embodiments of the present invention, a computer software product including a tangible non-transitory computer-readable medium in which program instructions are stored, which instructions, when read by a processor, cause the processor to define a bounding region on a screen. The instructions further cause the processor to render a quadric, which is defined in a parameter space, over a three-dimensional electroanatomical map of a surface of a heart that is displayed on the screen, by, for each pixel in the bounding region, transforming, to the parameter space, a virtual ray that passes through the pixel, and ascertaining whether a point of intersection between the transformed virtual ray and the quadric exists in the parameter space, and, for each pixel in the bounding region for which the point of intersection exists, rendering the pixel on the screen, based on properties of the point of intersection.

The present invention will be more fully understood from the following detailed description of embodiments thereof, taken together with the drawings, in which:

BRIEF DESCRIPTION OF THE DRAWINGS

FIG. 4 is a schematic illustration of a method for marking a silhouette of a quadric, in accordance with some embodiments of the present invention.

DETAILED DESCRIPTION OF EMBODIMENTS

Overview

Figure 1:
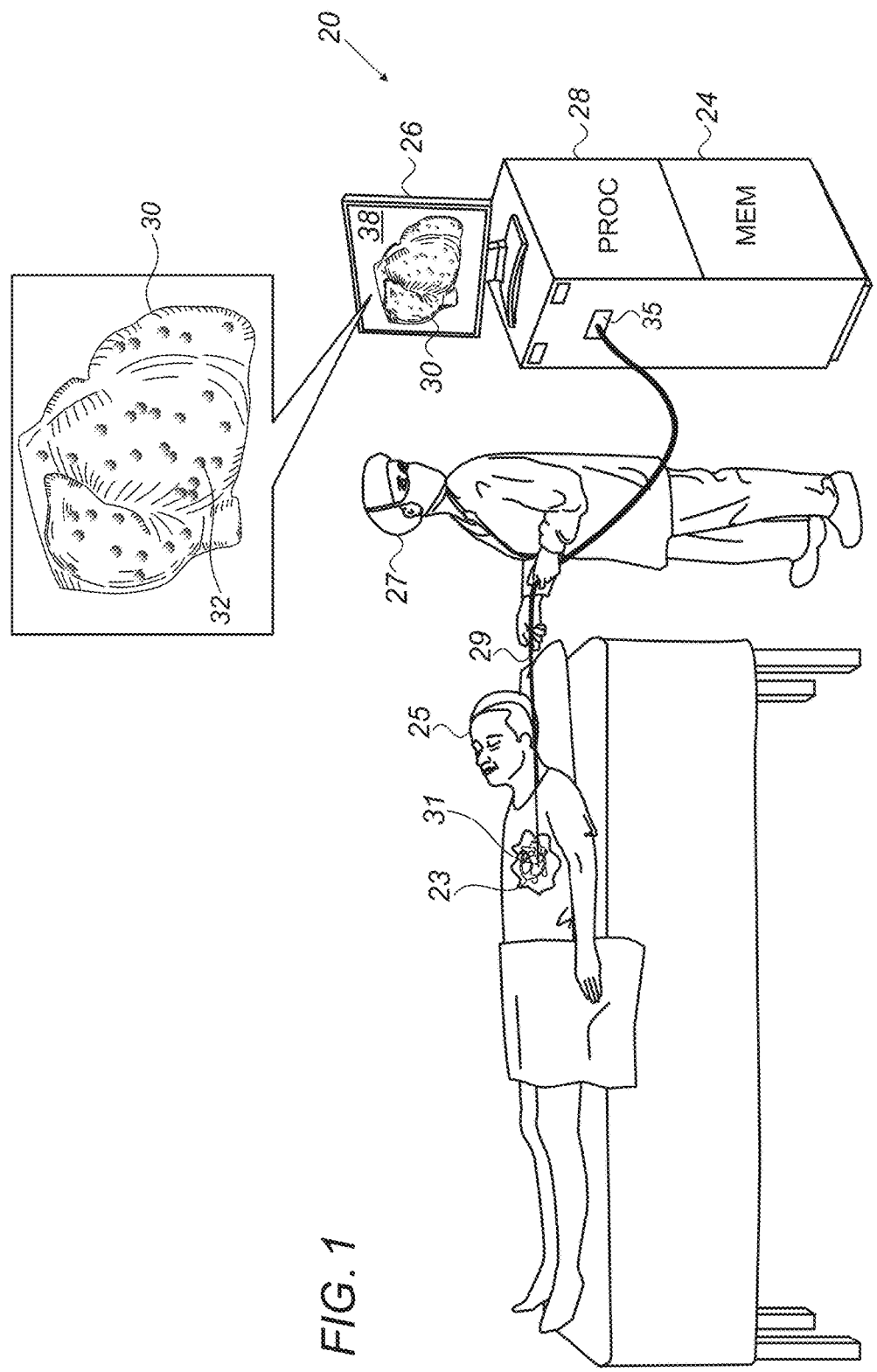
FIG. 1 is a schematic illustration of a system for rendering quadrics over an electroanatomical map, in accordance with some embodiments of the present invention.

In embodiments of the present invention, an electroanatomical map of a portion of a subject's heart is constructed, and is then rendered on-screen. (Such a map is typically embodied by a three-dimensional mesh that is constructed from a plurality of points that correspond to respective locations at which an electrical property was measured.) A plurality of quadrics may then be rendered over the electroanatomical map. For example, during and/or following an ablation procedure, each portion of cardiac tissue that has been ablated, or is presently being ablated, may be marked on-screen by a respective quadric, such as a sphere or an ellipse. Typically, the resolution of this marking is relatively high, such that, in some cases, it may be necessary to render a large number (e.g., tens of thousands) of quadrics on-screen.

Embodiments of the present invention provide improved methods and systems for rendering quadrics, such that a large number of quadrics may be quickly and accurately rendered. For example, the following algorithm may be used to render each of the quadrics:

(i) Define a diagonal matrix Q, which represents a quadric in parameter space (or "model space") that is centered at the origin and is bounded by a cube with corners at $(-1,-1,-1)$ and $(1,1,1)$. For example, a unit sphere of radius 1, centered at $(0,0,0)$, is represented by $$Q = \begin{matrix} 1 & 0 & 0 & 0 \\ 0 & 1 & 0 & 0 \\ 0 & 0 & 1 & 0 \\ 0 & 0 & 0 & -1 \end{matrix}.$$

(ii) Compute the matrix M, which, upon multiplying a point having homogenous coordinates $$\begin{matrix} x \\ y \\ z \\ 1 \end{matrix}$$

in parameter space, transforms the point such that the point is properly placed within the virtual scene, which exists in "world space." The matrix M thus represents a transformation from parameter space to world space.

(iii) Given the matrix V, which represents a transformation from world space to view space, and P, which represents a perspective or orthographic projection from view space to screen space (which is defined in terms of the coordinate system of the screen on which the quadric is rendered), compute the matrix T=PVM, which represents a transformation from parameter space to screen space. Also, compute $T^{-1}$, the inverse of T, which represents a transformation from screen space to parameter space.

(iv) Define, on the screen (i.e., screen space), a bounding region B that contains all of the pixels in which the quadric might be rendered. Typically, B is a bounding rectangle. (Some graphics processing units may require that this bounding rectangle be divided into two triangles.) Since the quadric is bounded in parameter space by the above-described cube, B may be computed by transforming the eight corners of the cube to screen space, and then finding the minimum bounding rectangle of these transformed corners.

(v) Perform the following steps for each pixel in B:

(v-a) From the matrix P, compute D and O, where O is the origin of a ray that passes through the pixel, and D is the direction vector of this ray. (For an orthographic projection, O will vary between the pixels, with D constant. For a perspective projection, D will vary between the pixels, with O constant.) Then transform O and D to parameter space, by multiplying each of these vectors by $T^{-1}$. The transformed ray may be expressed as $R'=O'+tD'$, where $O'=T^{-1}O$, and $D'=T^{-1}D$.

(v-b) In parameter space, find any points X' at which the transformed ray intersects the quadric. (If the ray does not intersect the quadric, move on to the next pixel in B.) If there is more than one point of intersection, choose the point X' that the ray collides with first. Also calculate the normal vector N' to the quadric at X'.

(v-c) Transform N' to view space, by multiplying N' by a "normal matrix" $M_N$ that is derived from V ($N=M_N N'$).

(v-d) Calculate the coloring of the pixel, based on the coloring of the quadric at point X' and the transformed normal vector N.

(It is noted that a plurality of pixels in bounding rectangle B may be processed, as described above, in parallel, e.g., by a graphics processing unit (GPU).)

An advantage of this algorithm is that, as described above, step (v-b) operates in parameter space, where the quadric is represented by a diagonal matrix Q. Since Q is diagonal, Q may be reduced to vector form. For example, assuming the notation for Q assumed above, a diagonal matrix Q may be represented by the vector $$Qd = \begin{matrix} A \\ E \\ H \\ J \end{matrix},$$

$Q_d$ being the diagonal of Q. The representation of Q in this manner leads to a faster computation of the points of intersection X'. In contrast, were step (v-b) to operate in view space, the computation would be slower, given that the multiplication of Q by M, V, and/or any other transformational matrix typically causes Q to cease to be a diagonal matrix.

More particularly, substituting the transformed ray equation $R'=O'+tD'$ into the quadric equation $X^T Q X=0$, one arrives at the quadratic equation $at^2+bt+c=0$, where $a=D'^T Q D'$, $b=2D'^T Q O'$, and $c=O'^T Q O'$. Hence, to find the intersections of the ray with the quadric, a, b, and c must be computed, following which the intersections may be found by solving for the roots of the above quadratic equation. Since these computations are performed in parameter space, however, $Q_d$ may be used to compute a, b, and c relatively quickly. For example, the computation of QO' may be performed by performing an element-wise multiplication of $Q_d$ with O', which involves only four multiplication operations. Moreover, since, in parameter space, Q is bounded by a cube with corners at $(-1,-1,-1)$ and $(1,1,1)$, various operations may be performed more quickly. For example, as described above, bounding region B may be computed relatively quickly, based on the projection of the corners of the cube onto the screen.

In contrast, were the intersection points not computed in parameter space, the computation of the equivalents of a, b, and c might involve a relatively large number of operations. For example, the computation of QO, assuming a non-diagonal matrix Q, involves computing the inner product of each of the rows of Q with O, requiring a total of 16 multiplication operations and 12 addition operations.

Embodiments described herein may be applied, for example, to the rendering of a sphere, ellipsoid, cylinder, cone, or hyperboloid, each of which may be represented by a diagonal matrix Q. Embodiments described herein may also be applied to the rendering of a paraboloid, in that, even though a paraboloid is not directly representable by a diagonal matrix, a paraboloid may be obtained by clipping an ellipsoid. Clipping may also be used to confine certain quadrics—such as cylinders, which extend to infinity—to the above-described cube in parameter space.

In some embodiments, the silhouette of a quadric (which may alternatively be referred to as the "outline" of the quadric) may be marked, e.g., to indicate that the quadric was selected by a user. Typically, this marking is performed while rendering the quadric. For example, for each transformed ray, the discriminant $b^2-4ac$ of the aforementioned quadratic equation $at^2+bt+c=0$ may be compared to zero. If the discriminant is greater than or equal to zero, indicating that an intersection point exists, the pixel may be rendered as described above. Otherwise, the distance between the transformed ray and the quadric may be estimated by solving the equation $b^2-4a(c+d)=0$ for d, and then taking $|d|$ as the estimated distance. If this estimated distance is less than a given threshold, the pixel may be marked to indicate the outline of the quadric.

Although the present application relates to the rendering of quadrics mainly in the context of electroanatomical maps, it is noted that embodiments described herein may be applied to any suitable quadric-rendering application. Moreover, the techniques described herein for marking the silhouette of a quadric may be performed even without performing all of the particular quadric-rendering techniques described herein. For example, even if the rays are not transformed to parameter space, the distances between the rays and the quadrics may be estimated as described herein, and the silhouette of the quadric may be marked responsively to these estimated distances.

System Description

Reference is initially made to FIG. 1, which is a schematic illustration of a system 20 for rendering quadrics over an electroanatomical map, in accordance with some embodiments of the present invention. One commercial product embodying elements of system 20 is the CARTO® 3 System, available from Biosense Webster, Inc. This system may be modified by those skilled in the art to embody the principles of embodiments described herein.

FIG. 1 illustrates an ablation procedure performed on a heart 23 of a subject 25, using an intrabody catheter 29. Catheter 29 comprises a distal end 31, comprising one or more ablating electrodes, and one or more tracking sensors (e.g., electromagnetic tracking sensors), which track the location of distal end 31. During the procedure, as a physician 27 moves distal end 31 along a surface (e.g., the inner or epicardial surface) of heart 23, the ablating electrodes pass ablating signals into the surface. While the procedure is ongoing, a processor (PROC) 28 receives, via an electrical interface 35 (comprising, for example, a port or other connector), signals from the tracking sensors, which indicate the locations of distal end 31. Processor 28 stores these locations in a computer memory (MEM) 24.

During, and/or following, the ablation procedure, processor 28 retrieves, from computer memory 24, a three-dimensional electroanatomical map 30 of the cardiac surface, and then renders map 30 on a screen 38 of a display 26. As described in detail below, the processor further renders a plurality of quadrics 32 over the map. Typically, each of the quadrics is rendered over a respective portion of the map that correspond to a location of distal end 31 during the procedure, as indicated by the location sensors. For example, a respective quadric may mark each location at which the distal end of the catheter ablated tissue of the subject. In other words, the processor may render quadrics over respective portions of the map corresponding to respective locations of distal end 31, in response to ablating signals being passed into the surface of the heart, by distal end 31, at the respective locations.

The rendering of quadrics over map 30, as described herein, may be performed in real-time, to help guide the physician during the procedure, and/or following the procedure, to facilitate a post-procedural assessment.

In general, processor 28 may be embodied as a single processor, or as a cooperatively networked or clustered set of processors. Processor 28 is typically a programmed digital computing device comprising a central processing unit (CPU) and/or a GPU, random access memory (RAM), non-volatile secondary storage, such as a hard drive or CD ROM drive, network interfaces, and/or peripheral devices. (In general, any of the tasks described herein as being performed by processor 28 may be performed by either a CPU or a GPU, or by both a CPU and a GPU, cooperatively.) Program code, including software programs, and/or data, are loaded into the RAM for execution and processing by the CPU and/or GPU, and results are generated for display, output, transmittal, or storage, as is known in the art. (Program code and/or data from the RAM may be stored in a separate memory belonging to the GPU, prior to use thereof by the GPU.) The program code and/or data may be downloaded to the processor in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Figure 2:
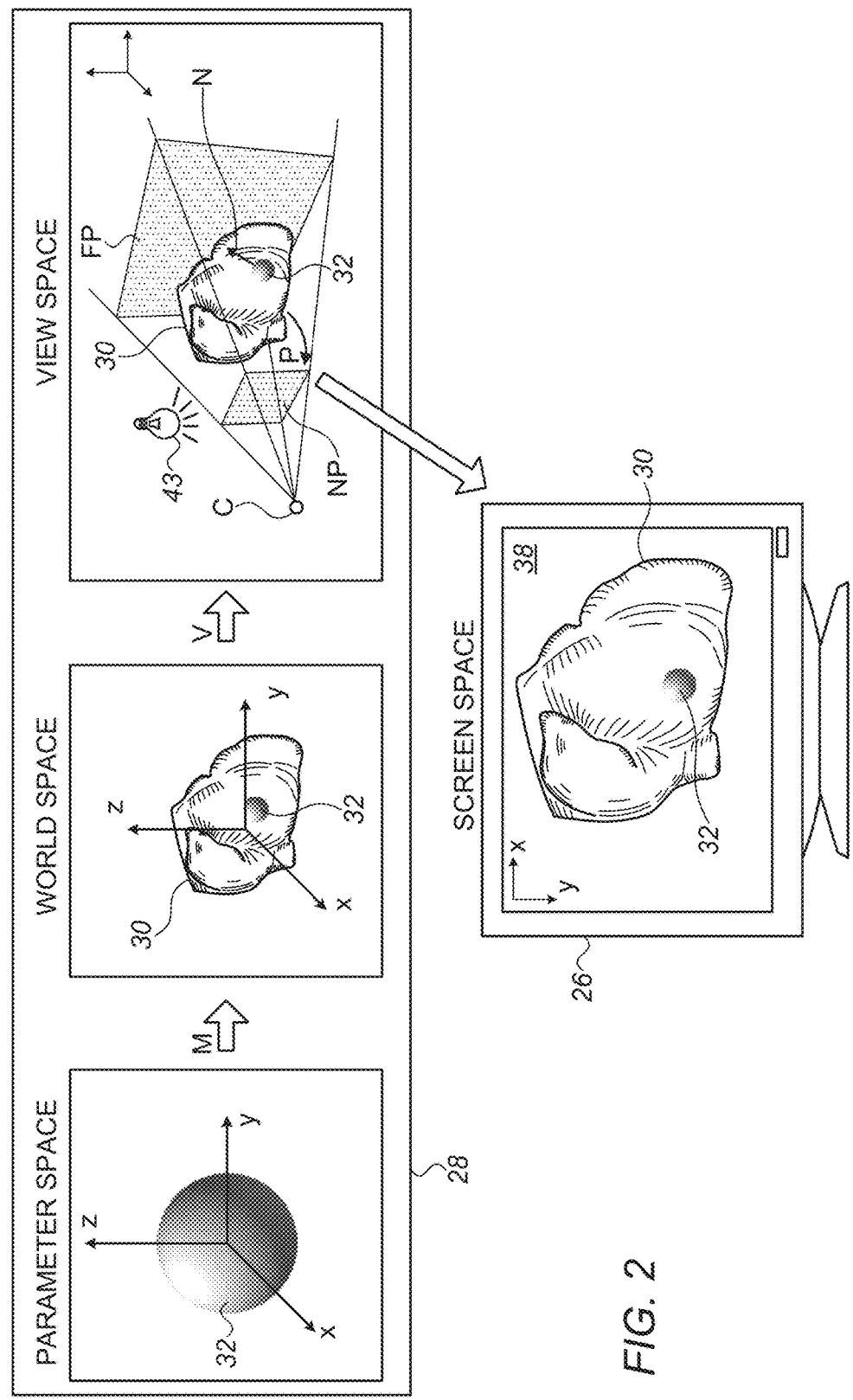
FIG. 2 is a schematic overview of a method for rendering a quadric, in accordance with some embodiments of the present invention.

Reference is now made to FIG. 2, which is a schematic overview of a method for rendering a quadric 32, in accordance with some embodiments of the present invention.

FIG. 2 depicts several "spaces," each of which is defined in terms of a respective coordinate system. Several of these spaces are virtual spaces that are defined by processor 28. In particular:

(i) Parameter space is a virtual three-dimensional space in which virtual objects to be rendered are defined in isolation.

(ii) World space is a virtual three-dimensional space in which objects defined in parameter space are suitably oriented, sized, and placed with respect to other objects in the virtual scene that is to be rendered. A matrix M transforms objects from parameter space to world space, by rotating, scaling, and/or translating these objects.

(iii) View space is a virtual three-dimensional space in which the virtual scene from world space, while being illuminated by a virtual light source 43, is imaged by a virtual camera, located at a camera location C. First, the virtual scene is placed between the near plane NP of the camera and the far plane FP of the camera (which may be located at infinite distance from the camera), in accordance with a transformation matrix V, which transforms the virtual scene from world space. Then, the processor causes the virtual camera to image the virtual scene, by projecting the scene onto near plane NP in accordance with a projection matrix P.

Near plane NP of the virtual camera is represented, in the real world, by screen 38; in other words, the virtual scene is rendered on screen 38 in accordance with the view of the virtual camera in view space. Coordinates of pixels belonging to screen 38 are defined in terms of a two-dimensional screen space. The above-described projection matrix P determines the location in screen space at which an object in view space is rendered, as well as the size and orientation of the rendered object. (Hence, projection matrix P may be said to represent a transformation from view space to screen space, as described above in the Overview.) The color with which the object is rendered is determined by the "objective" color of the object (as defined, typically, in parameter space), relevant properties of (such as the position and intensity of) virtual light source 43, and the normal vector N to the object, which affects the manner in which the object is illuminated by the virtual light source.

In accordance with the particular ray-casting techniques described below, the projection of objects onto near plane NP (and hence onto the screen) is accomplished by passing a plurality of virtual rays through the near plane (or equivalently, through the screen). Each of these virtual rays has a ray origin, which coincides with camera location C, and a ray-direction vector, each of which is derived from projection matrix P. As the virtual rays collide with objects in the virtual scene, the objects are projected onto the near plane, and are hence rendered on-screen.

FIG. 2 shows a particular example, whereby the processor defines a quadric 32 in parameter space, transforms the quadric to world space such that the quadric is placed over an electroanatomical map 30, images map 30 and quadric 32 in view space, and, finally, renders map 30 and quadric 32 on-screen. Aspects of this process are described in more detail immediately below, with reference to FIG. 3.

Figure 3:
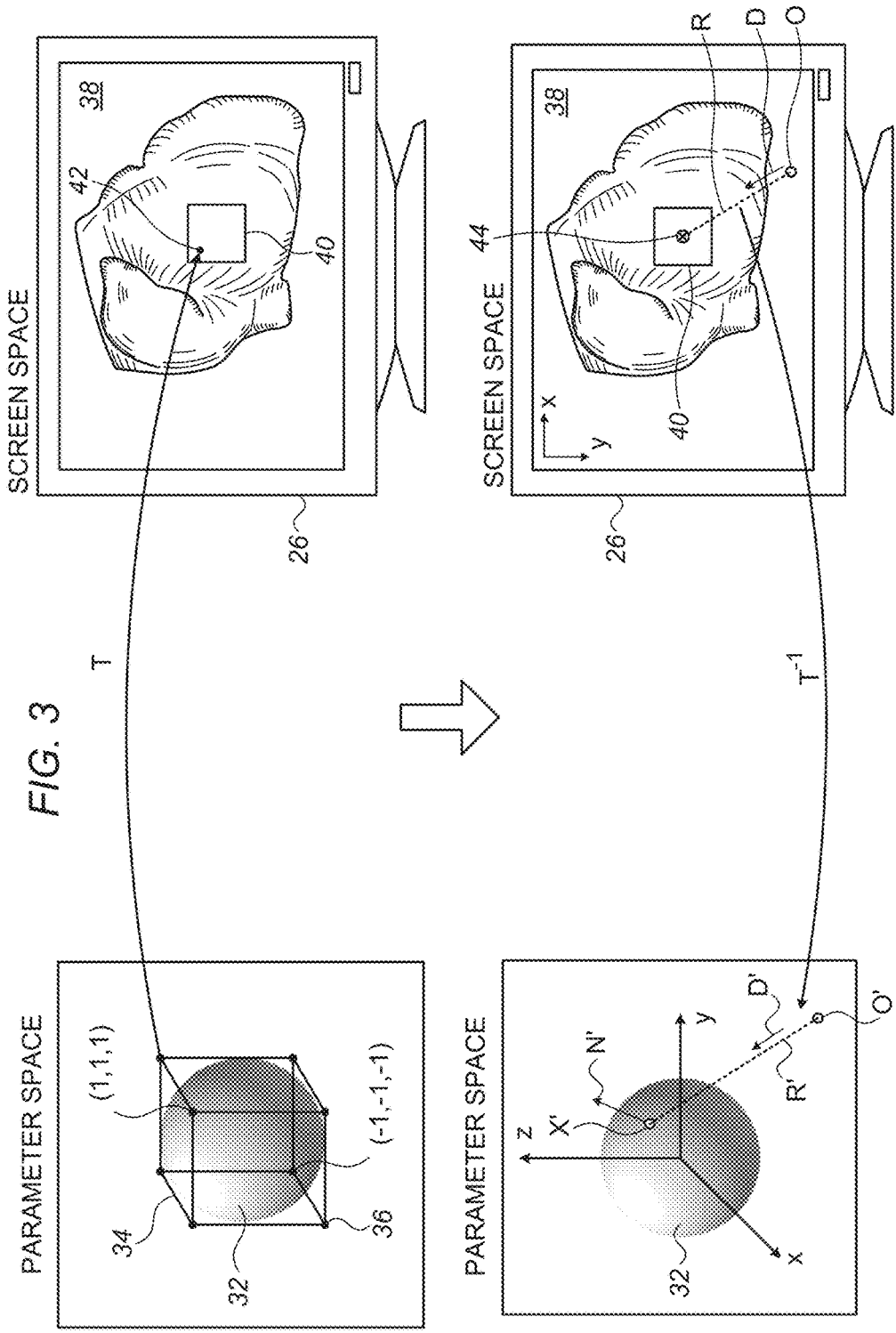
FIG. 3 is a schematic illustration of aspects of a method for rendering a quadric, in accordance with some embodiments of the present invention.

Reference is now made to FIG. 3, which is a schematic illustration of aspects of a method for rendering a quadric, in accordance with some embodiments of the present invention.

As described above with reference to FIG. 2, the processor first defines quadric 32 in parameter space, which is defined in terms of an (x,y,z) coordinate system. As described above in the Overview, the quadric is typically defined such that it is bounded by a cube 34 having eight corners 36, two of which are at (−1,−1,−1) and (1,1,1), respectively. As further described above in the Overview, the quadric is typically defined such that it is representable by a 4×4 diagonal matrix Q. For example, as shown in FIG. 3, the processor may define a sphere of radius 1 centered at the origin, which is representable by the diagonal matrix Q=

$$\begin{pmatrix} 1 & 0 & 0 & 0 \\ 0 & 1 & 0 & 0 \\ 0 & 0 & 1 & 0 \\ 0 & 0 & 0 & -1 \end{pmatrix}.$$

In addition to defining the shape and size of the quadric, the processor defines the coloring of the quadric. For example, the processor may make the quadric uniformly colored. (Typically, the quadric is defined in accordance with values stored in memory 24, and/or in accordance with relevant input from a user.)

As further shown in FIG. 3, display 26 comprises a screen 38, comprising a plurality of pixels, each of which has (x,y) coordinates within the screen space of the screen. To render quadric 32 on the screen 38, the processor first defines a bounding region 40 on the screen, i.e., in screen space. (Typically, the defined bounding region is not displayed on the screen.) As described above in the Overview, to define bounding region 40, the processor typically first transforms corners 36 of the cube to screen space. This is shown, in FIG. 3, for one of the corners 36, whereby the matrix T, upon multiplying the parameter-space $$\begin{matrix} x \\ y \\ z \\ 1 \end{matrix}$$

coordinates of the corner, transforms the corner to its new (x,y) coordinates in screen space, indicated in FIG. 3 by a transformed corner 42. After thus transforming each of corners 36 to screen space, the processor defines bounding region 40 such that the bounding region is a minimum bounding rectangle of the transformed corners 42.

Next, as shown in the lower portion of FIG. 3, the processor iterates over each pixel 44 in bounding region 40, and, if appropriate, renders the pixel as part of the quadric. In particular, for each pixel 44, the processor first transforms, from the screen space to the parameter space, a virtual ray R that passes through the pixel. As described above in the Overview and with reference to FIG. 2, virtual ray R has a ray origin O, which is located in front of the screen (at the position of the virtual camera in view space), and a ray-direction vector D, which describes the direction, into the screen, of the virtual ray. (As described above, the virtual ray is thus described by the equation R=O+tD.) The processor transforms this virtual ray by computing O', which is the ray origin O transformed to parameter space, and D', which is the ray-direction vector D transformed to parameter space. To compute O' and D', the processor multiplies O and D, respectively, by $T^{-1}$, the inverse of the transformation matrix T.

The transformation of the virtual ray yields a transformed virtual ray R' in parameter space, described by the equation R'=O'+tD'. Following this transformation, the processor ascertains whether a point of intersection between the transformed virtual ray and the quadric exists in the parameter space, by attempting to compute a point of intersection X' between transformed virtual ray R' and quadric 32. In other words, the processor attempts to identify a point X' in parameter space at which the transformed virtual ray collides with the quadric. Provided that such a point of intersection X' exists, the processor then renders pixel 44 on screen 38, as further described below, based on properties of point of intersection X', such as the color of the quadric, and normal to the quadric, at point X'.

As described above in the Overview, the computation of point of intersection X' is relatively quick, given that the processor performs this computation in parameter space. For example, the processor may quickly compute each of the coefficients a=$D'^T Q D'$, b=$2D'^T Q O'$, and c=$O'^T Q O'$, by representing Q as a four-element vector $Q_D$, and then performing an element-wise multiplication of $Q_D$. The processor may then solve, for the parameter t, the equation $at^2+bt+c=0$. Writing this solution (or "root") as $t_R$, the point of intersection X may then be computed as $O'+t_R D'$ (Typically, the equation $at^2+bt+c=0$ will have two positive roots, indicating that the virtual ray intersects the quadric at two points. In such a case, the processor chooses the point of intersection that is closer to the origin of the ray.)

For example, the processor may represent the unit sphere by $$Q_D = \begin{matrix} 1 \\ 1 \\ 1 \\ -1 \end{matrix},$$

which is the diagonal of the matrix Q for the unit sphere. Then, assuming that $$O' = \begin{matrix} Ox \\ Oy \\ Oz \\ Ow \end{matrix} \text{ and } D' = \begin{matrix} Dx \\ Dy \\ Dz \\ Dw \end{matrix},$$

the processor may compute the first coefficient a by performing an element-wise multiplication of $Q_D$ with D', yielding the vector $$\begin{matrix} Dx \\ Dy \\ Dz \\ -Dw \end{matrix},$$

and then left-multiplying this vector by $D'^T$, yielding $Dx^2+Dy^2+Dz^2-Dw^2$. Likewise, for the second coefficient b and third coefficient c, the processor may perform an element-wise multiplication of $Q_D$ with O', yielding the vector $$\begin{matrix} Ox \\ Oy \\ Oz \\ -Ow \end{matrix},$$

and then left-multiply this vector by $2D'^T$ and $O'^T$, respectively. The processor may then solve the equation $at^2+bt+c=0$, as described above.

Typically, along with computing the point of intersection X', the processor computes the normal vector N' to the quadric at the point of intersection. Then, following the computation of the point of intersection X' and the corresponding normal vector N', the processor transforms normal vector N' to view space, by left-multiplying N' by VM, yielding a transformed normal vector N. The processor then renders pixel 44, based on the coloring of the quadric at the point of intersection X', and the transformed normal vector N (which, as described above with reference to FIG. 2, influences the manner in which light from the virtual light source interacts with the quadric).

Reference is now made to FIG. 4, which is a schematic illustration of a method for marking a silhouette of a quadric, in accordance with some embodiments of the present invention.

In some embodiments, the silhouette 70 of one or more quadrics 32 may be marked on screen 38. For example, subsequently to various quadrics being rendered on-screen as described above, a user may select one of the quadrics, e.g., by hovering a mouse pointer 68 over the quadric and then clicking the mouse. Subsequently, while the quadric is re-rendered, silhouette 70 may be marked, to indicate that the quadric was selected.

As noted above with reference to FIG. 1, processor 28 typically comprises a GPU, configured to perform the rendering of quadrics as described herein. Typically, the GPU continually refreshes the screen at relatively short intervals; for example, the GPU may refresh the screen—and, in so doing, re-render all of the relevant quadrics on-screen—60 times per second. Hence, advantageously, the silhouette of the quadric is marked immediately following the selection of the quadric, without any delay that is noticeable to the user. Alternatively or additionally to continually refreshing the screen, the GPU may, in response to the user selecting a given quadric, immediately refresh the screen, or at least re-render the selected quadric, such that the silhouette is immediately marked.

To mark the silhouette while rendering the quadric, the processor casts transformed virtual rays R', corresponding to respective pixels in bounding box 40, as described above with reference to FIG. 3. For each ray, the processor ascertains whether the ray intersects the quadric. If yes, the processor renders the appropriate pixel to show a portion of the quadric, as described above with reference to FIG. 3. Otherwise, the processor estimates the shortest distance d0 between the quadric and the ray, i.e., the distance between the quadric and the point on the ray that is closest to the quadric. If the estimate of d0 is less than a given threshold distance, the processor marks the corresponding pixel as belonging to the silhouette, i.e., the processor marks the pixel to indicate that the pixel is at the edge of the quadric, in that the pixel is within the threshold distance of the quadric. For example, the processor may color the pixel to indicate that the pixel belongs to the silhouette of the quadric.

In general, since the width of the marking (in screen space) is a function of the threshold distance (in parameter space), the threshold distance may be set to any suitable value, responsively to the desired width of the marking. For example, for a quadric bound by cube 34 (which has corners at $(-1,-1,-1)$ and $(1,1,1)$), the threshold may be between 0.01 and 0.2.

Typically, to check whether the ray intersects the quadric, the processor ascertains whether the above-described quadratic equation $at^2+bt+c=0$ has any real roots, by computing the discriminant $b^2-4ac$ of the equation, and then checking if this discriminant is greater than or equal to zero. If yes, the processor ascertains that the ray intersects the quadric, and therefore proceeds to render the pixel as described above with reference to FIG. 3. Otherwise (i.e., if the discriminant is negative), the processor ascertains that the ray does not intersect the quadric. In response thereto, the processor estimates distance d0, by setting a modified discriminant $b^2-4a(c+d)$, where $|d|$ approximates d0, to 0, and then solving for d. In particular, by solving $b^2-4a(c+d)=0$, the processor estimates d0 as $|b^2/4a-c|$, i.e., the absolute value of $b^2/4a-c$.

Figure 5A:
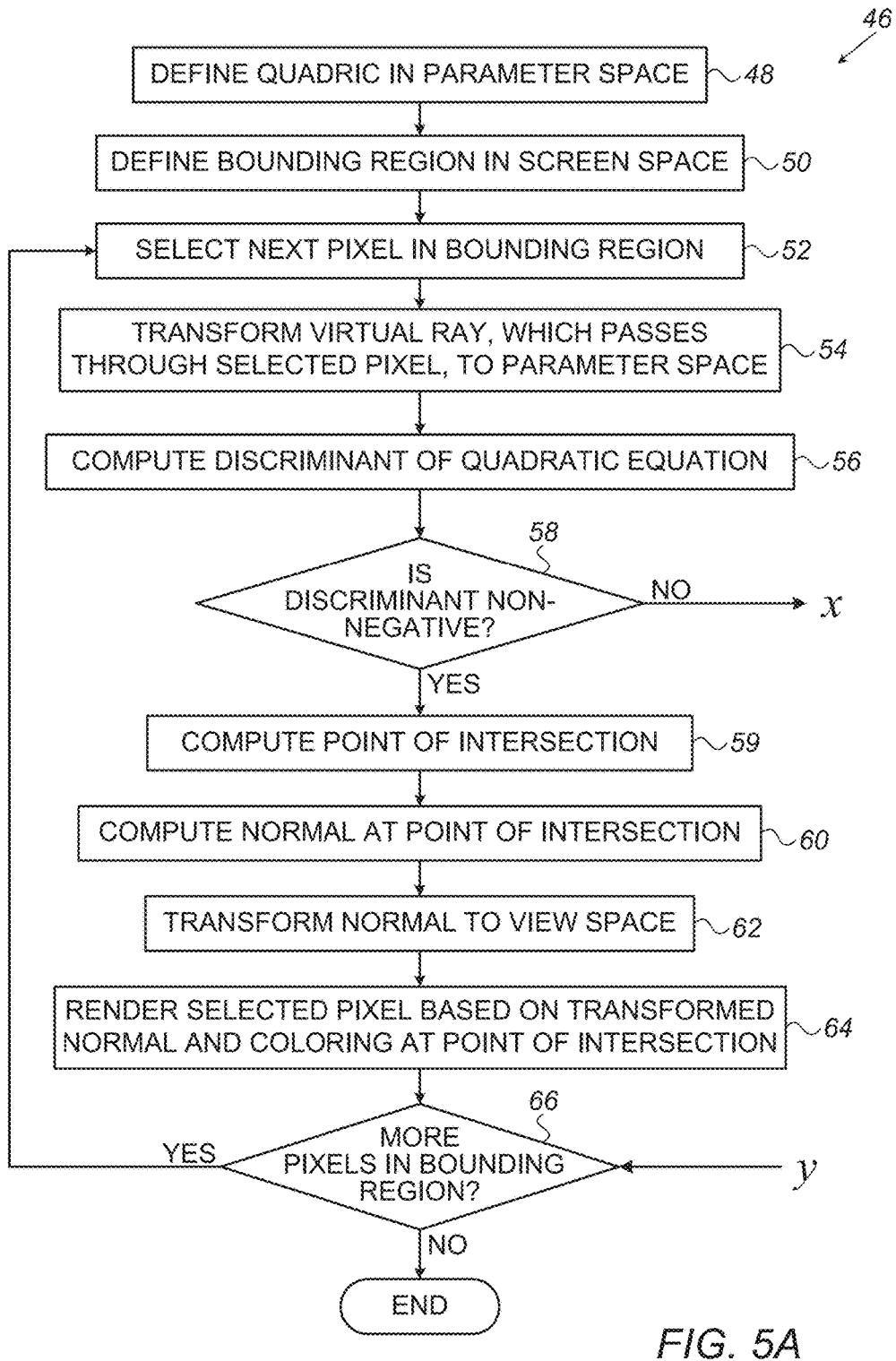
FIGS. 5A-B collectively show a flow diagram for a rendering method performed by a processor, in accordance with some embodiments of the present invention.
Figure 5B:
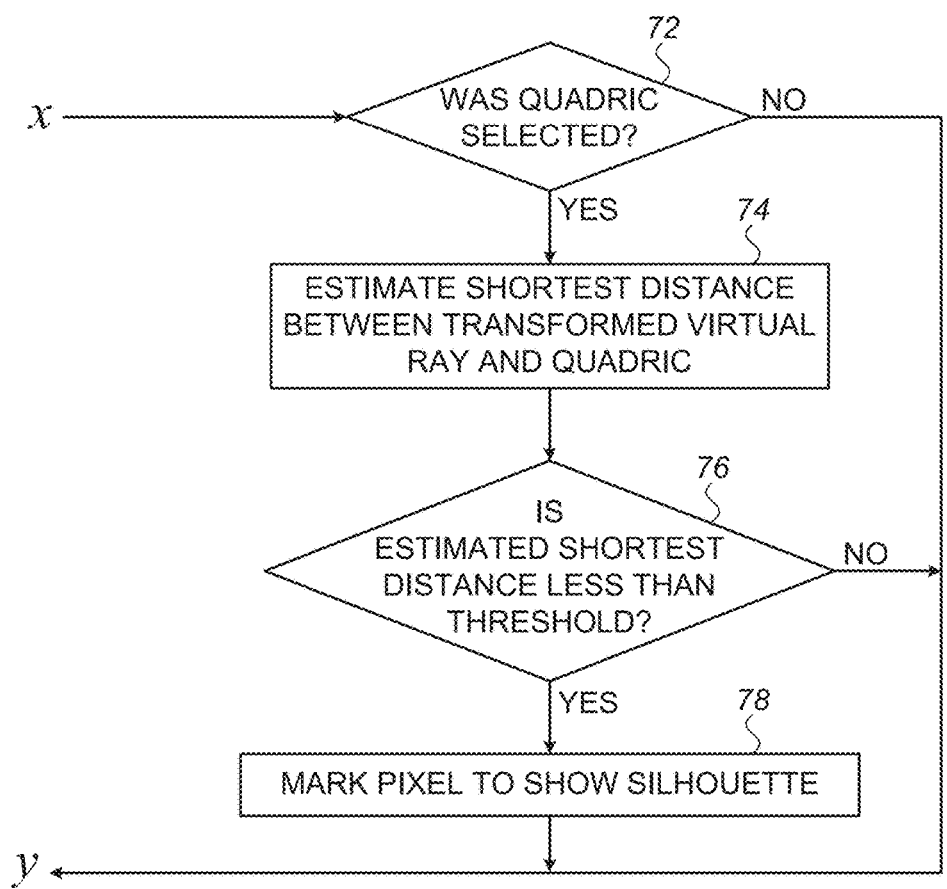

Reference is now made to FIGS. 5A-B, which collectively show a flow diagram for a rendering method 46 performed by processor 28, in accordance with some embodiments of the present invention. (In general, the various steps of method 46 were already described above, but are again presented in brief with reference to FIG. 4.)

First, at a quadric-defining step 48, the processor defines the quadric, which is to be rendered, in parameter space. Next, at a bounding-region-defining step 50, the processor defines a suitable bounding region in screen space. This bounding region is typically the smallest region that can be computed within a reasonable amount of time and that contains all of the pixels that might correspond to a portion of the quadric. For example, as described above with reference to FIG. 3, the bounding region may be computed as the minimum bounding rectangle of the transformed corners of a cube that contains the quadric in parameter space.

Next, the processor begins to iterate over all of the pixels in the bounding region. At the start of each iteration, at a pixel-selecting step 52, the processor selects a pixel that has not yet been processed. Next, at a ray-transforming step 54, the processor transforms a virtual ray, which passes through the selected pixel, to parameter space. Subsequently, at a discriminant-computing step 56, the processor computes the discriminant of the equation $at^2+bt+c=0$. Next, at a first checking step 58, the processor checks if the discriminant is non-negative. If yes, the processor, at an intersection-point-computing step 59, computes the point of intersection between the ray and the quadric. Following (or in conjunction with) the computation of the point of intersection, the processor, at a normal-computing step 60, computes the normal to the quadric at the point of intersection. Next, at a normal-transforming step 62, the processor transforms the normal to view space. Finally, at a rendering step 64, the processor renders the selected pixel, based on the transformed normal and the coloring of the quadric at the point of intersection.

Following the rendering of the pixel, the processor, at a second checking step 66, checks if more unprocessed pixels remain in the bounding region. If yes, the processor processes the next pixel. Otherwise, method 46 ends. (If additional quadrics are to be rendered, however, method 46 may be repeated for each of the additional quadrics.)

Returning now to first checking step 58, if the discriminant is negative (indicating that $at^2+bt+c=0$ has only imaginary roots), the processor does not render the selected pixel as part of the quadric. Instead (as shown in FIG. 5B), the processor checks, at a third checking step 72, whether the quadric that is being rendered was selected by the user. If not, the processor proceeds to second checking step 66. Otherwise, the processor, at an estimating step 74, estimates the shortest distance between the transformed virtual ray and the quadric. Subsequently, at a fourth checking step 76, the processor checks if the estimated shortest distance is less than a particular threshold. If yes, the processor, at a marking step 78, marks the pixel to show the silhouette. Subsequently to marking the pixel, or if the estimated shortest distance is not less than the threshold, the processor proceeds to second checking step 66.

As described above in the Overview, in some embodiments, multiple pixels in the bounding region are processed in parallel, e.g., by a GPU belonging to processor 28. For example, all of the pixels in the bounding region may be processed in parallel, such that pixel-selecting step 52 is performed no more than once by each thread that is executed by the processor, and second checking step 66 is not necessarily performed at all.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus, comprising:
a display, comprising a screen; and
a processor, configured:
to define a bounding region on the screen,
to render a quadric, which is defined in a parameter space, over a three-dimensional electroanatomical map of a surface of a heart that is displayed on the screen, by:
for each pixel in the bounding region, transforming, to the parameter space, a virtual ray that passes through the pixel, and ascertaining whether a point of intersection between the transformed virtual ray and the quadric exists in the parameter space, and
for each pixel in the bounding region for which the point of intersection exists, rendering the pixel on the screen, based on properties of the point of intersection; and
to mark a silhouette of the quadric on the screen, by, for each pixel in the bounding region for which the point of intersection does not exist:
estimating a shortest distance between the transformed virtual ray and the quadric, and
provided that the estimated shortest distance is less than a threshold, marking the pixel as belonging to the silhouette.

2. The apparatus according to claim 1, wherein the processor is configured to mark the silhouette of the quadric in response to a user selecting the quadric on the screen.

3. The apparatus according to claim 1, wherein, for each pixel in the bounding region for which the point of intersection does not exist, the processor is configured to:
ascertain that the point of intersection does not exist, by:
substituting an equation of the transformed virtual ray into an equation of the quadric, such as to yield a quadratic equation $at^2+bt+c=0$, and
ascertaining that a discriminant $b^2-4ac$ of the quadratic equation is negative, and
in response to ascertaining that the point of intersection does not exist, estimate the shortest distance between the transformed virtual ray and the quadric as $|c-b^2/4a|$.

4. The apparatus according to claim 1, wherein the processor is further configured to define the quadric, in the parameter space, such that the quadric is bounded by a cube having eight corners, two of which are at $(-1,-1,-1)$ and $(1,1,1)$, respectively.

5. The apparatus according to claim 4, wherein the processor is configured to define the bounding region by:
transforming the corners of the cube to a screen space, which is defined in terms of a coordinate system of the screen, and
defining the bounding region such that the bounding region is a minimum bounding rectangle of the transformed corners.

6. The apparatus according to claim 1, wherein the processor is further configured to define the quadric such that the quadric is representable by a 4×4 diagonal matrix Q.

7. The apparatus according to claim 6,
wherein the virtual ray has a ray origin O and a ray-direction vector D,
wherein the processor is configured to transform the virtual ray by computing O', which is the ray origin O transformed to the parameter space, and D', which is the ray-direction vector D transformed to the parameter space, and
wherein the processor is configured to ascertain whether the point of intersection exists by:
computing a first coefficient $a=D'^T QD'$, where $D'^T$ is a transpose of D', a second coefficient $b=2D'^T QO'$, and a third coefficient $c=O'^T QO'$, and
subsequently, ascertaining whether a quadratic equation $at^2+bt+c=0$ has any real roots.

8. The apparatus according to claim 7, wherein the processor is further configured to represent Q as a four-element vector $Q_D$, and wherein the processor is configured to compute each of the first coefficient a, the second coefficient b, and the third coefficient c by performing an element-wise multiplication of $Q_D$.

9. The apparatus according to claim 1, wherein the processor is further configured to receive a signal that indicates a location of a distal end of an intrabody catheter, and wherein the processor is configured to render the quadric over a portion of the three-dimensional electroanatomical map that corresponds to the indicated location.

10. The apparatus according to claim 9, wherein the processor is configured to render the quadric in response to an ablating signal being passed into the surface of the heart, by the distal end of the intrabody catheter, at the indicated location.

11. The apparatus according to claim 1, wherein the processor is configured to render the pixel on the screen by:
computing a normal vector to the quadric at the point of intersection, and
rendering the pixel, based on a coloring of the quadric at the point of intersection, and the normal vector.

12. A method, comprising:
using a processor, defining a bounding region on a screen;
rendering a quadric, which is defined in a parameter space, over a three-dimensional electroanatomical map of a surface of a heart that is displayed on the screen, by:
for each pixel in the bounding region, transforming, to the parameter space, a virtual ray that passes through the pixel, and ascertaining whether a point of intersection between the transformed virtual ray and the quadric exists in the parameter space, and
for each pixel in the bounding region for which the point of intersection exists, rendering the pixel on the screen, based on properties of the point of intersection; and
marking a silhouette of the quadric on the screen, by, for each pixel in the bounding region for which the point of intersection does not exist:
estimating a shortest distance between the transformed virtual ray and the quadric, and
provided that the estimated shortest distance is less than a threshold, marking the pixel as belonging to the silhouette.

13. The method according to claim 12, wherein marking the silhouette of the quadric comprises marking the silhouette of the quadric in response to a user selecting the quadric on the screen.

14. The method according to claim 12, wherein estimating the shortest distance between the transformed virtual ray and the quadric comprises estimating the shortest distance between the transformed virtual ray and the quadric by, for each pixel in the bounding region for which the point of intersection does not exist:

ascertaining that the point of intersection does not exist, by:
  substituting an equation of the transformed virtual ray into an equation of the quadric, such as to yield a quadratic equation $at^2+bt+c=0$, and
  ascertaining that a discriminant $b^2-4ac$ of the quadratic equation is negative, and
in response to ascertaining that the point of intersection does not exist, estimating the shortest distance between the transformed virtual ray and the quadric as $|c-b^2/4a|$.

15. The method according to claim 12, further comprising defining the quadric, in the parameter space, such that the quadric is bounded by a cube having eight corners, two of which are at $(-1,-1,-1)$ and $(1,1,1)$, respectively.

16. The method according to claim 15, wherein defining the bounding region comprises:
  transforming the corners of the cube to a screen space, which is defined in terms of a coordinate system of the screen, and
  defining the bounding region such that the bounding region is a minimum bounding rectangle of the transformed corners.

17. The method according to claim 12, further comprising defining the quadric such that the quadric is representable by a 4×4 diagonal matrix Q.

18. The method according to claim 17,
wherein the virtual ray has a ray origin O and a ray-direction vector D,
wherein transforming the virtual ray comprises transforming the virtual ray by computing O', which is the ray origin O transformed to the parameter space, and D', which is the ray-direction vector D transformed to the parameter space, and
wherein ascertaining whether the point of intersection exists comprises:
  computing a first coefficient $a=D'^TQD'$, where $D'^T$ is a transpose of D', a second coefficient $b=2D'^TQO'$, and a third coefficient $c=O'^TQO'$, and
  subsequently, ascertaining whether a quadratic equation $at^2+bt+c=0$ has any real roots.

19. The method according to claim 18, further comprising representing Q as a four-element vector $Q_D$, wherein computing the first coefficient a, the second coefficient b, and the third coefficient c comprises computing each of the first coefficient a, the second coefficient b, and the third coefficient c by performing an element-wise multiplication of $Q_D$.

20. The method according to claim 12, further comprising receiving a signal that indicates a location of a distal end of an intrabody catheter, wherein rendering the quadric comprises rendering the quadric over a portion of the three-dimensional electroanatomical map that corresponds to the indicated location.

21. The method according to claim 20, wherein rendering the quadric comprises rendering the quadric in response to an ablating signal being passed into the surface of the heart, by the distal end of the intrabody catheter, at the indicated location.

22. The method according to claim 12, wherein rendering the pixel on the screen comprises:
  computing a normal vector to the quadric at the point of intersection, and
  rendering the pixel, based on a coloring of the quadric at the point of intersection, and the normal vector.

23. A computer software product comprising a tangible non-transitory computer-readable medium in which program instructions are stored, which instructions, when read by a processor, cause the processor:
  to define a bounding region on a screen,
  to render a quadric, which is defined in a parameter space, over a three-dimensional electroanatomical map of a surface of a heart that is displayed on the screen, by:
    for each pixel in the bounding region, transforming, to the parameter space, a virtual ray that passes through the pixel, and ascertaining whether a point of intersection between the transformed virtual ray and the quadric exists in the parameter space, and
    for each pixel in the bounding region for which the point of intersection exists, rendering the pixel on the screen, based on properties of the point of intersection; and to mark a silhouette of the quadric on the screen, by, for each pixel in the bounding region for which the point of intersection does not exist:
      estimating a shortest distance between the transformed virtual ray and the quadric, and
      provided that the estimated shortest distance is less than a threshold, marking the pixel as belonging to the silhouette.

24. The computer software product according to claim 23, wherein the instructions further cause the processor:
  to compute a normal vector to the quadric at the point of intersection, and
  to render the pixel, based on a coloring of the quadric at the point of intersection, and the normal vector.

* * * * *